United States Patent [19]

Plank et al.

[11] 4,021,502

[45] May 3, 1977

[54] CONVERTING LOW MOLECULAR WEIGHT OLEFINS OVER ZEOLITES

[75] Inventors: Charles J. Plank, Woodbury; Edward J. Rosinski, Pedricktown; Edwin N. Givens, Pitman, all of N.J.

[73] Assignee: Mobil Oil Corporation, New York, N.Y.

[22] Filed: Feb. 24, 1975

[21] Appl. No.: 552,487

[52] U.S. Cl. .............. 260/683.15 R; 260/683.43; 260/683.64
[51] Int. Cl.² ........................................ C07C 3/20
[58] Field of Search ............ 260/683.15 R, 683.64, 260/683.43

[56] References Cited

UNITED STATES PATENTS 3,775,501   11/1973   Kaeding et al. .................. 260/673

*Primary Examiner*—C. Davis
*Attorney, Agent, or Firm*—Charles A. Huggett; Raymond W. Barclay; Claude E. Setliff

[57] ABSTRACT

Gaseous $C_2$–$C_5$ olefins, either alone or in admixture with paraffins having 1 to 5 carbon atoms, are converted into gasoline blending stock with a good research octane number by passage over ZSM-4, ZSM-12, ZSM-18, chabazite or Zeolite beta.

8 Claims, No Drawings

CONVERTING LOW MOLECULAR WEIGHT OLEFINS OVER ZEOLITES

BACKGROUND OF THE INVENTION

1. Field of of the Invention

This invention relates to a method of catalytically converting olefins into gasoline fractions by passing such olefins over a crystalline aluminosilicate zeolite.

2. Brief Description of the Prior Art

It has long been known to contact various hydrocarbon fractions with acidic catalysts generally and, in particular, with solid siliceous acidic catalysts — including those referred to as crystalline aluminosilicate zeolites. Contact of said hydrocarbon feed with said acid catalysts was carried out for a wide variety of reactions including cracking, isomerization, hydrocracking, etc. Representative United States Patents disclosing and claiming contacting of various hydrocarbon fractions with crystalline aluminosilicates are U.S. Pat. No. 3,140,249; 3,140,251; 3,140,253; and 3,140,322.

The contact of paraffinic feedstocks with crystalline aluminosilicate zeolites is also known in the art, and the primary reason for contacting paraffinic materials with zeolites has been for the purpose of cracking them, i.e. converting them to lower molecular weight products. Typical applications in this general field would be the use of crystalline aluminosilicate zeolites for carrying out dewaxing reactions, i.e. the cracking of paraffins to low molecular weight materials. United States Pat. No. 3,400,072 discloses a dewaxing process with crystalline aluminosilicates generally and U.S. Pat. No. 3,700,585 discloses and claims dewaxing operations carried out with crystalline aluminosilicates identified as those of the ZSM-5 type.

The instant application is not concerned with hydrocarbon conversion in general, but rather, is concerned with the conversion of a hydrocarbon feed consisting essentially of $C_2$–$C_5$ olefins, mixtures thereof with $C_1$–$C_5$ paraffins. Additionally, the instant application is not concerned primarily with the cracking of these materials to still lower molecular weight products, but rather is concerned primary with the preparation of higher molecular weight olefins from the stated feed and low conversion to aromatics.

SUMMARY OF THE INVENTION

The invention provides a process for producing a gasoline blending stock, said process comprising contacting a $C_2$–$C_5$ olefin, mixtures thereof or mixtures thereof with paraffins having from 1 to 5 carbon atoms with a crystalline aluminosilicate zeolite selected from ZSM-4, ZSM-12, ZSM-18, chabazite and Beta at a WHSV of from about 0.2 to about 50, preferably 0.5 to 10, and at a temperature of from about 450° to about 1200° F, preferably about 550° to about 900° F.

DESCRIPTION OF SPECIFIC EMBODIMENTS

The present invention is concerned with contacting a feed stream consisting essentially of $C_2$–$C_5$ olefins, mixtures thereof and mixtures thereof with $C_1$–$C_5$ paraffins with a crystalline alumiosilicate zeolite to obtain predominantly higher molecular weight olefins which have good octane numbers and which are excellent gasoline blending stocks. Olefin product can be maximized by operating under conditions that give low yields of aromatics.

Other conditions of the process are:

1. temperatures between about 450° and about 1200°, preferably between about 550° and about 1000° F;

2. weight hour space velocity (WHSV) between about 0.2 and about 50, preferably between about 1 and about 25; and 3. hydrocarbon partial pressure between about 0.1 to about 50 atmospheres, preferably between about 0.3 and about 20 atmospheres.

By maintaining the process within the stated parameters, a high level of activity can be realized with a catalyst which would otherwise not be useful from a commercial standpoint. Stated another way, the process of this invention has a very practical economic potential since the zeolite employed under the stated reaction conditions is surprisingly stable. It therefore will remain active over long periods of time, thereby eliminating the need for frequent regeneration.

As has heretofore been stated the novel process of this invention utilizes crystalline aluminosilicates, specifically ZSM-4, ZSM-12, ZSM-18, chabazite and Zeolite Beta.

ZSM-4 is disclosed fully in British Pat. No. 1,117,568. ZSM-12 and ZSM-18 are respectively disclosed in U.S. Pat. No. 3,832,449 and U.S. application 365,020, filed May 29, 1973, all of which are incorporated herein by reference for all they disclose concerning the synthesis and chemical and physical properties of the mentioned zeolites. Chabazite and Zeolite Beta are well known. The latter zeolite is described in U.S. Pat. No. 3,308,069, also incorporated herein by reference. Zeolite Beta will, for the purpose of this invention, have a $SiO_2/Al_2O_3$ ratio of from about 5 to about 100, preferably from about 5 to about 80.

ZSM-18 can conveniently be prepared by heating in an aqueous solution a mixture of oxides or of materials whose chemical composition can be represented as mixtures of $Na_2O$, $Al_2O_3$, $SiO_2$, $H_2O$ and T, wherein T represents 1 mole of a trisquaternary ammonium hydroxide which is preferably 1,3,4,6,7,9-hexahydro-2,2,5,5,5,8,8-hexamethyl-2H-benzo [1,2-C:-3,4-C': 5,6-C''] tripyrolium trihydroxide. The heating can be carried out from about 20° to about 150° C for a period of time ranging from 2 to 150 days.

The composition of the reaction mixture, expressed in terms of mole ratios of oxides is as follows

| | Broad | Preferred |
|---|---|---|
| $SiO_2/Al_2O_3$ | 10–30 | 15–18 |
| $Na_2O/Al_2O_3$ | .2–5 | 1–2 |
| $H_2O/Al_2O_3$ | 200–1500 | 400–700 |
| $T/Al_2O_3$ | 1–10 | 1–3 |

The product which crystallizes from the hot reaction mixture is separated, suitably by centrifuging or filtration, and is washed with water until the effluent wash water in equilibrium with the zeolite has a pH of from about 9 to 12. The material so obtained is thereafter activated by heating in an inert atmosphere at a temperature in the approximate range of 100° to 600° C.

In making zeolite ZSM-18, the usual method comprises reacting, in aqueous media, sodium aluminate or an amorphous sodium aluminosilicate gel with a solution prepared by addition of colloidal silica to a solution of tris-quaternary ammonium hydroxide. The reaction is carried out in a suitable vessel made, for example, of metal or glass and capable of closure to prevent loss of water. The reaction mixture is initially continuously or periodically stirred to insure homogeneity. After this mixing, agitation may be stopped as it is unnecessary to agitate the reaction mass during the formation and crystallization of the zeolite, although mixing during such later stages has not been found to be detrimental.

The crystallization procedures can be satisfactorily carried out at temperatures within the range from about 35° to about 200° C. The pressure during crystallization is atmospheric or at least that corresponding to the vapor pressure of water in equilibrium with the mixture of reactants, while temperatures as low as about 35° C may be employed. Such lower temperatures require a long reaction period. Preferably, a temperature of approximately 60° to 150° c is employed and heating is continued until the desired crystalline zeolite product is formed. The zeolite crystals, are then separated from the mother liquor and washed, preferably with distilled water, until the effluent wash water in equilibrium with the product has a pH of between about 9 and about 12.

In the synthesis of zeolite ZSM-18, it has been found that the composition of the reaction mixture is critical. Specifically, the presence of tris-quaternary ammonium ions in such mixture has been found to be essential for the production of zeolite ZSM-18. In the absence of such ions no zeolite ZSM-18 was obtained. The crystallization temperature and the length of time the crystallization temperature is maintained are important variables in determining the yield of crystalline material. Under some conditions, for example, too low a temperature for too short a time, no crystalline product is realized. Extreme conditions may also result in the formation of materials other than zeolite ZSM-18.

It has been found furthermore, that if the silica to alumina ratio in the forming solution is below 10, i.e. 9 (all other factors being equal), that ZSM-18 will be formed but that it will either be obtained in admixture with other zeolites and/or that it will be unstable at elevated temperatures. If the silica to alumina ratio of the forming solution is maintained within the above set out limits, a pure and stable ZSM-18 will be obtained.

Sodium oxide present in the reaction mixture may be derived from sodium aluminate or an amorphous sodium aluminosilicate gel. The latter is characterized by the following composition:

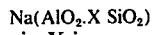

wherein X is a number in the approximate range of 0.2 to 20. This material may be prepared by reaction of methyl orthosilicate and sodium aluminate. Another suitable source of alumina and sodium oxide is a solution of aluminum turnings in sodium hydroxide. Silicate present in the reaction mixture may be derived from a variety of sources, for example, aqueous sodium silicates, silica gel, silica hydrosol, and silicate esters. Thus, silica is desirably introduced into the reaction mixture as a colloidal suspension.

The zeolites used in the instant invention usually have a certain proportion of the original cations associated therewith replaced by a wide variety of other cations according to techniques well known in the art. Typical replacing cations include hydrogen, ammonium and metal cations including mixtures of the same.

Of the replacing cations, particular preference is given to hydrogen, ammonium, rare earth, and mixtures thereof.

Typical ion exchange techniques involve contacting the particular zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. No. 3,140,249; 3,140,251; and 3,140,253.

Following contact with the ion exchange solution of the desired replacing cation, the zeolite may be washed with water and dried at a temperature ranging from 150° F to about 600° F and thereafter heated in air or other suitable gas at temperatures ranging from about 500° F to 1500° F for periods of time ranging from 1 to 48 hours or more.

It is also possible to treat the zeolite with steam at elevated temperatures ranging from about 800° F to about 1600° F and preferably about 1000° F and about 1500° F, if such is desired. The treatment may be accomplished in atmospheres consisting partially or entirely of steam.

A similar treatment can be accomplished at lower temperatures and elevated pressures, e.g. 350°–700° F at 10 to about 200 atmospheres.

One embodiment of this invention resides in the use of a porous matrix with the zeolites previously described. The zeolites can be combined, dispersed or otherwise intimately admixed with a porous matrix in such proportions that the resulting product contains from 1% to 95% by weight, and preferably from 20% to 80% by weight, of the zeolite in the final composite.

The term "porous matrix" includes active or inactive inorganic compositions with which the aluminosilicates can be combined, dispersed or otherwise intimately admixed. It is to be understood that the porosity of the compositions employed as a matrix can either be inherent in the particular material or it can be introduced by mechanical or chemical means. Representative matrices which can be employed include metals and alloys thereof, sintered metals and sintered glass, asbestos, silicon carbide aggregates, pumice, firebrick, diatomaceous earths, and inorganic oxides. Inorganic compositions especially those of a siliceous nature are preferred. Of these matrices, inorganic oxides such as clay, chemically treated clay, silica, silica-alumina, etc., are particularly preferred because of their superior porosity, attrition resistance and stability.

Compositing an aluminosilicate with an inorganic oxide can be achieved by several methods wherein the aluminosilicates are reduced to a particle size less than 40 microns, preferably less than 10 microns, and intimately admixed with an inorganic oxide while the latter is in a hydrous state such as in the form of hydrosol, hydrogel, wet gelatinous precipitate, or in a dried state, or a mixture thereof. Thus, finely divided aluminosilicates can be mixed directly with a siliceous gel formed by hydrolyzing a basic solution of alkali metal silicate with an acid such as hydrochloric, sulfuric, acetic, etc. Mixing of the three components can be accomplished in any desired manner, such as in a ball mill or other such device. The aluminosilicates also may be dispersed in a hydrosol obtained by reacting an alkali metal silicate with an acid or alkaline coagulant. The hydrosol is then permitted to set in mass to a hydrogel which is thereafter dried and broken into pieces of desired shape or dried by conventional spray drying techniques or dispersed through a nozzle into a bath of oil or other water-immiscible suspending medium to obtain spheriodally shaped "bead" particles of catalyst such as described in U.S. Pat. No. 2,384,946. The aluminosilicate siliceous gel thus obtained is washed free of soluble salts with water and thereafter dried and/or calcined as desired.

Similarly, the aluminosilicates may be incorporated with an aluminiferous oxide. These are gels or hydrous oxides and are well known in the art. They may be prepared, for example, by adding ammonium hydroxide, ammonium carbonate, and the like, to a salt of aluminum, such as aluminum chloride, aluminum sulfate or aluminum nitrate, in an amount sufficient to form aluminum hydroxide which, upon drying, is converted to alumina. The aluminosilicate may be incorporated with the aluminiferous oxide while the latter is in the form of hydrosol, hydrogel, or wet gelatinous precipitate or hydrous oxide, or in the dried state.

The inorganic oxide may also consist of raw clay or a clay mineral which has been treated with an acid medium to render it active. The aluminosilicate can be incorporated into the clay simply by blending the two and fashioning the mixture into desired shapes. Suitable clays include attapulgite, kaoline, sepiolite, polygarskite, kaolinite, halloysite, plastic ball clays, bentonite, montmorillonite, illite, chlorite, etc.

Other useful matrices include powders of refractory oxides, such as alumina, alpha alumina, etc., having very low internal pore volume. Preferably, these materials with respect to the instant reactions, having substantially no inherent catalytic activity of their own.

The catalyst product can be heated in steam or in other atmospheres, e.g. air, near the temperature contemplated for conversion but may be heated to operating temperatures initially during use in the conversion process. Generally, the catalyst is dried between about 150° and about 600° F. It may thereafter be calcined in air, steam, nitrogen, helium flue gas, or other gases not harmful to the catalyst product, at temperatures ranging from about 500° F to 1600° F and for periods of time ranging from 1 to 48 hours or more. It is to be understood that the aluminosilicate can also be calcined prior to incorporation into the inorganic oxide gel. It is to be further understood that the aluminosilicate or aluminosilicates need not be ion exchanged prior to incorporation into a matrix but can be so treated during or after such incorporation.

The feedstock useful in the present process may be a pure $C_2$–$C_5$ olefin, or it may be prepared by forming mixtures thereof and mixtures with $C_1$–$C_5$ paraffins. It may in addition be any of a number of feeds from other sources. These include total gas streams from, for example, an FCC, TCC or Riser cracking unit, a $C_3$— dry gas fraction from the same or different source, a $C_4$ mixture from an unsaturated gas plant, a gas stream from a coking unit and a gas stream from a pyrolysis unit.

ILLUSTRATIVE EXAMPLES

The following Examples will illustrate the invention. It is to be understood they are merely illustrative and are not to be construed as limiting the scope of the invention. Parts are parts by weight unless otherwise stated.

EXAMPLE 1

This ZSM-4 sample was prepared by first reacting the following components to form the ZSM-4.

Solution A
  119.3 parts $Al_2(SO_4)_3 \cdot 14H_2O$
  33.7 parts $H_2SO_4$ (98%)
  276.2 parts $H_2O$
  Sp. Gr. 1.237 at 77° F.

Solution B
  174.4 parts 50% NaOH
  298.0 parts $H_2O$
  34.4 parts TMACl 50% Solution (tetramethylammonium chloride)
  652.0 parts Q Brand sodium silicate 28.9 Wt.% $SiO_2$ 8.9 Wt.% $Na_2O$ 62.2 Wt.% $H_2O$
  Sp. Gr. 1.306 at 73° F These solutions were mixed together through a mixing nozzle flowing solution A at 5800 cc/min. and solution B at 1980 cc/min. This mixture was held in a steam jacketed vessel at about 210°–214° F at static condition for a total of 69 hours, during which time the crystalline ZSM-4 product formed.

The resulting crystalline product was separated from the unreacted solution by filtration and washing.

The composition of the ZSM-4 product was as follows:

| | |
|---|---|
| $SiO_2$ | 72.5 Wt.% |
| $Al_2O_3$ | 18.7 Wt.% |
| Na | 7.3 Wt.% |

The sodium form of ZSM-4 was further base exchanged four times with 200 parts of 25% by weight $(NH_4)_2SO_4$ solution heated to 140°–170° F by contacting for 1–2 hours. The batch was filtered each time prior to reslurrying with a fresh batch of base exchange solution. Finally, the slurry was washed three times with hot water by the filtering and reslurrying method. The washed product was dried at 230° F.

The composition of the processed ZSM-4 product was

| | |
|---|---|
| $SiO_2$ | 80.4 Wt.% |
| $Al_2O_3$ | 21.1 Wt.% |
| Na | 0.35 Wt.% |

This product had a cyclohexane sorption capacity of 4.6 Wt.% and a water capacity of 16.2 Wt.%. The product at this point was 90 crystalline ZSM-4.

In preparing the particular extruded catalyst used in this invention, 659 parts of the ZSM-4 (80.5% solids at 1000° F), prepared as described above, was mixed with 825 parts of hydrated alumina (34.7 Wt.% solids at 1000° F) and 10 Wt.% organic fiber material, Solka Floc No. 40. The ZSM-4 was first dispersed with 81.6 parts of the solka Floc and about 130 parts of water in a high shear mixer and then was added to the alumina. The total composite was mixed together in a muller mixer. It was necessary to add about 250 parts of water at this point to reach the extrudable texture.

The moist mixture was then extruded in a hydraulic press requiring a 6–9 ton pressure to force the mix through one thirty-secondth inch holes. The resulting extrudate was then dried at 230° F over a weekend, sized to about one-fourth inch length and then calcined 10 hours at 900° F and 4 hours at 1000° F with a 5% oxygen stream using an air-nitrogen gas.

The activated extrudate had a surface area of 347m²/g, a residual sodium of 0.25 Wt.%, and was 45% crystalline ZSM-4 by X-ray.

This catalyst was used in the evaluation described on Page 18.

EXAMPLE 2

This sample of ZSM-12 was prepared by interacting the following components and solutions.

Solution A
  6 parts $NaAlO_2$ (41.8% $Al_2O_3$ 33.4% $Na_2O$)
  17.5 parts NaOH (77.5% $Na_2O$)

Solution B
  100 parts TEABr (tetraethylammonium bromide)
  350 parts $H_2O$

Solution C
  500 parts Ludox colloidal Silica (30% Wt. $SiO_2$)

These were mixed together adding A to B, followed by adding C to mixed A and B. The components were mixed 5 minutes in a high shear mixer and transferred to a polypropylene jar and placed in a steam bath at 212° F. This mixture was held in the steam bath for 91 days, allowing the ZSM-12 to crystallize. The resulting product was separated from the liquor by filtration and water washing with 4 liters of water. The ZSM-12 product was air dried at 230° F and then was analyzed. The composition was as follows:

| | | |
|---|---|---|
| N | 1.08 Wt.% | (Solids 86.4 Wt.% at 1000° F) |
| Na | 0.56 Wt.% | |
| $Al_2O_3$ | 2.16 Wt.% | |
| $SiO_2$ | 93.6 Wt.% | |

After calcining the product for 17 hours at 1000° F, it had the following sorption properties:

| | |
|---|---|
| Water | 10.9 Wt.% |
| Cyclohexane | 12.0 Wt.% |
| n-hexane | 9.9 Wt.% |

This ZSM-12 was further processed by first heating it for 3 hours at 700° F to remove the organics and then by base exchanging with 5% $NH_4Cl$ solution at 190° F using 10 ml of solution per gram of thermally treated ZSM-12. Four one-hour contacts with fresh 5% $NH_4Cl$ solution were employed. The mixture of solution and ZSM-12 was stirred during the base exchange procedure. Following the base exchange treatment, the ZSM-12 was washed free of chloride ion, air dried at 230° F, pelleted and sized 14 to 25 mesh, and then calcined 10 hours at 1000° F in air.

The activated HZSM-12 was then used in the evaluation presented on page 18.

EXAMPLE 3

ZSM-18 was prepared in accordance with the following:

Preparation of a Tris-quarternary Ammonium Bromide

The reaction vessel employed was a three-liter, four-neck, round bottom flask, equipped with stirrer, reflux condenser, thermometer and gas inlet. Dimethylamine gas was passed through a 5A molecular sieve drying column into a vigorously stirred suspension of 254.4 parts of hexabromomethylbenzene in 631 parts of absolute ethanol which is maintained at 70° C. After several hours of passing dimethylamine, a 1 cc sample was taken into a test tube and water added to it. (At some point, the entire suspension becomes water soluble. This point depends on the rate of stirring, gas-bubbling, and the like, and will generally be between 5 and 20 hours). The yield was 200-220 parts (theoretical: 216 parts of 1,3,4,6,7,9-hexahydro-2,2,5,5,8,8-hexamethyl-2H-benzol[1,2-C:3,4-C':5,6-C] tripyrolium tribromide) which had a purity, by Mohr bromide titration of 70–90%. Without further purification, the material was used to prepare hydroxide via ion-exchange.

Preparation of tris-quaternary ammonium hydroxide

Into a Dowex-1 resin bed (2.5 inch diameter, 20 inch high) having a capacity of 2.5 gram equivalent weights (gew.) was passed 2 gew of the tribromide prepared as set forth above. The amount used was 350 g, calculated on the basis of 100% pure product. About 3 liters of a 0.6–0.7 N alkaline solution was obtained. This amounted to a recovery of 90% of input material. The tris-quaternary ammonium hydroxide has the following formula:

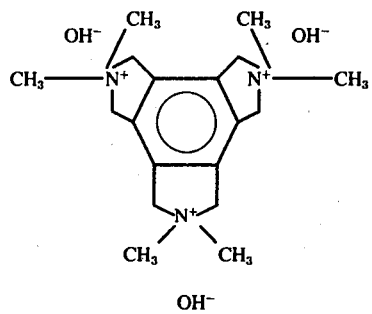

7.05 grams of sodium aluminate was dissolved in 277 ml of 0.65 N tris-quaternary ammonium hydroxide prepared in accordance with the above and 13.5 ml of water. To the clear aluminate solution was added 68.5 grams of tetramethylorthosilicate and the resulting mixture stirred vigorously until a gel formed.

The gel had the following composition:

(2 T) — 1.14 $Na_2O$ — $Al_2O_3$ — 15 $SiO_2$ — 500 $H_2O$ wherein T represents 1 mol of the tris-quaternary ammonium hydroxide.

The above gel was placed in a pressure bomb and heated for five days at 125–130° C. The product was filtered and washed and identified by X-ray analysis as being substantially pure ZSM-18.

The ZSM-18 obtained has the following formula:

1.06 T(2/3) O: 0.09 $Na_2O$ : $Al_2O_3$ : 10.6 $SiO_2$ wherein T represents a tris-quaternary ammonium cation. The zeolite is stable upon heating a 1000° for three hours.

EXAMPLE 4

Zeolite β and the ammonium form thereof were prepared as follows:

4.28 parts of sodium aluminate (41.8% $Al_2O_3$; 31.3% $Na_2O$) and 8.25 parts of sodium hydroxide were dissolved in 175 parts of water. To this was added 50 parts of tetraethylammonium bromide. To this solution was added 250 parts of colloidal $SiO_2$ (30% $SiO_2$) and the resulting mixture was stirred for 15 minutes. The gel which formed had the following composition:

13.6 $(C_2H_5)_4^+$ : 7.5 $Na_2O$ : $Al_2O_3$ : 70 $SiO_2$ : 1100 $H_2O$

The gel was placed in a plastic jar and heated for 111 days at 210° F. The resulting product was filtered and washed and was identified by X-ray analysis as a crystalline Beta type zeolite. The Beta zeolite had the following composition:

3.42 $(TEA)_2{}^*O$ : 0.72 $Na_2O$ : $Al_2O_3$ : 82.2 $SiO_2$

*tetraethylammonium Other zeolite Beta samples prepared had $SiO_2$./$Al_2O_3$ ratios ranging from 5 to about 82.

40 grams of the above product were contacted 3 times with 800 ml of a 5% solution of $NH_4Cl$ at 210° F for 2 hours each contact and 2 times for 1.5 hours each contact. The reaction mixture was not stirred, the product was washed, chlorine-free, was dried at 230° F calcined at 1000° F for 10 hours and was used in the evaluation described hereinbelow.

EXAMPLE 5

The chabazite (25 parts) used was prepared by subjecting Nova Scotia chabazite to 5-1 hour exchanges at 190° F with 0.5 N $NH_4Cl$ (10 cc/gm. of zeolite), water washed until chloride free, drying at 230° F (Na content at this point 0.14% by weight pelleted and sized to 14 to 25 mesh particles) and then calcined at 1000° F for ten hours, the temperature being raised to 1000° F at the rate of 2° per minute.

EVALUATION

The following catalysts were tested for their oligomerization activity and for their ability to produce liquid oligomer products. The feed was prolylene and the temperature and pressure were 600° F and 0 psig. Following are the results.

| Catalyst | WHSV | Wt.% Liquid Product from Charge | Refractive Index |
|---|---|---|---|
| Example 1 | 0.8 | 38 | 1.4139 |
| Example 2 | 1.72 | 79.8 | 1.4354 |
| HZSM-18 | 0.79 | 44.7 | 1.4139 |
| Example 4 | 0.81 | 52.2 | 1.4416 |
| Example 5 | 0.84 | 39.7 | 1.4142 |

It is evident from the refractive indexes shown in the above data that the aromatic content of the products is low. As tables of representative hydrocarbons show, paraffins and olefins through $C_9$ have refractive indexes less than 1.420. Aromatics, in contrast, have mush larger values between 1.49 and 1.50.

We claim:

1. A process for producing a gasoline or a gasoline blending stock, the process comprising passing a feedstock consisting essentially of a $C_2$–$C_5$ olefin, mixtures of such olefins or mixtures of such olefins with $C_1$–$C_5$ paraffins over ZSM-4, ZSM-18 or Chabazite at a temperature of from about 450° F to about 1200° F, a WHSV of from about 0.2 to about 50 and a hydrocarbon partial pressure of from about 0.1 to about 50 atmospheres.

2. The process of claim 1 wherein the zeolite is ZSM-4.

3. The process of claim 1 wherein the zeolite is ZSM-18.

4. The process of claim 1 wherein the zeolite is Chabazite.

5. The process of claim 1 wherein a portion of the original cations associated with the zeolite are replaced by another cation.

6. The process of claim 1 wherein the zeolite is combined with a matrix.

7. The process of claim 1 wherein the olefin is propylene.

8. The process of claim 1 wherein the zeolite is steamed prior to use in the process.

* * * * *

UNITED STATES PATENT AND TRADEMARK OFFICE
CERTIFICATE OF CORRECTION

PATENT NO. : 4,021,502

DATED : May 3, 1977

INVENTOR(S) : CHARLES J. PLANK, EDWARD J. ROSINSKI and EDWIN N. GIVENS

It is certified that error appears in the above-identified patent and that said Letters Patent are hereby corrected as shown below:

Column 2, line 36, "purpose" should read --purposes--.
Column 3, line 9, "later" should read --latter--.
Column 3, line 19, "150°c" should read --150°C--.
Column 6, line 53, "90 crystalline" should read --90% crystalline--
Column 8, line 58, "1000°" should read --1000°F--.
Column 9, line 28, "chloride" should read --chlorine--.
Column 9, line 39, "proylene" should read --propylene--.
Column 10, line 15, "mush" should read --much--.

Signed and Sealed this

Seventh Day of February 1978

[SEAL]

Attest:

RUTH C. MASON
Attesting Officer

LUTRELLE F. PARKER
Acting Commissioner of Patents and Trademarks